(12) United States Patent
Ootsuka et al.

(10) Patent No.: US 8,927,237 B2
(45) Date of Patent: Jan. 6, 2015

(54) METHOD FOR PRODUCING ACYLOXYPYRANONE COMPOUND, METHOD FOR PRODUCING ALKYNE COMPOUND, AND METHOD FOR PRODUCING DIHYDROFURAN COMPOUND

(75) Inventors: Yoshikazu Ootsuka, Funabashi (JP); Tomohiro Akeboshi, Funabashi (JP); Akiko Yamazaki, Funabashi (JP); Yusuke Iriyama, Funabashi (JP)

(73) Assignee: Nissan Chemical Industries, Ltd., Tokyo (JP)

( * ) Notice: Subject to any disclaimer, the term of this patent is extended or adjusted under 35 U.S.C. 154(b) by 93 days.

(21) Appl. No.: 13/639,437

(22) PCT Filed: Apr. 7, 2011

(86) PCT No.: PCT/JP2011/058835
§ 371 (c)(1),
(2), (4) Date: Oct. 4, 2012

(87) PCT Pub. No.: WO2011/126082
PCT Pub. Date: Oct. 13, 2011

(65) Prior Publication Data
US 2013/0023018 A1    Jan. 24, 2013

(30) Foreign Application Priority Data
Apr. 7, 2010  (JP) ................. 2010-088819

(51) Int. Cl.
C12P 17/06 (2006.01)
C12P 17/04 (2006.01)
C07F 7/08 (2006.01)
C07D 307/33 (2006.01)
C07B 53/00 (2006.01)
C07D 309/30 (2006.01)
C07D 309/32 (2006.01)

(52) U.S. Cl.
CPC .............. *C07D 307/33* (2013.01); *C07B 53/00* (2013.01); *C07D 309/30* (2013.01); *C07D 309/32* (2013.01); *C07F 7/083* (2013.01); *C12P 17/04* (2013.01); *C12P 17/06* (2013.01)
USPC ............................ 435/125; 435/126; 549/214

(58) Field of Classification Search
CPC ......... C07B 53/00; C07F 7/083; C12P 17/06; C12P 17/04
USPC ................... 435/125, 126; 549/214
See application file for complete search history.

(56) References Cited

U.S. PATENT DOCUMENTS

2010/0280235 A1   11/2010   Nagai et al.

FOREIGN PATENT DOCUMENTS

JP       2006-528972 A    12/2006
WO    WO 2005/011709 A1   2/2005
WO    WO 2009/084655 A1   7/2009

OTHER PUBLICATIONS

International Search Report issued in PCT/JP2011/058835 mailed Jul. 12, 2011.
Maddaford A. et al., "Stereoselective synthesis of rac-4'-ethynyl-2'-deoxy-and 4'-ethynyl-2',3'-dideoxy-2',3'-didehydronucleoside analogues", Synthesis, 2007, pp. 1378-1384, No. 9.
van den Heuvel, M. et al., "Optically active 6-Acetyloxy-2H-pyran-3(6H)-one obtained by Lipase Catalyzed Transesterification and Esterification", Tetrahedron Letters, 1997, pp. 1655-1658, vol. 38, No. 9.

*Primary Examiner* — Chih-Min Kam
(74) *Attorney, Agent, or Firm* — Birch, Stewart, Kolasch & Birch, LLP

(57) ABSTRACT

An acylating agent and a hydrolase are caused to act on a hydroxypyranone represented by formula (I) in a water-containing organic solvent, to thereby produce an acyloxypyranone compound represented by formula (II) (wherein $R^1$ represents an acyl group). Then, an acetylene organic metal compound represented by formula (III) (wherein $R^2$ represents a hydrogen atom or a tri-substituted silyl group, and M represents an alkali metal atom, aluminum, or a magnesium monohalide) and a coordinating additive are caused to act on the acyloxypyranone compound represented by formula (II), to thereby produce an alkyne compound represented by formula (IV). The alkyne compound represented by formula (IV) is hydrolyzed with acid, to thereby produce a dihydrofuran compound represented by formula (V).

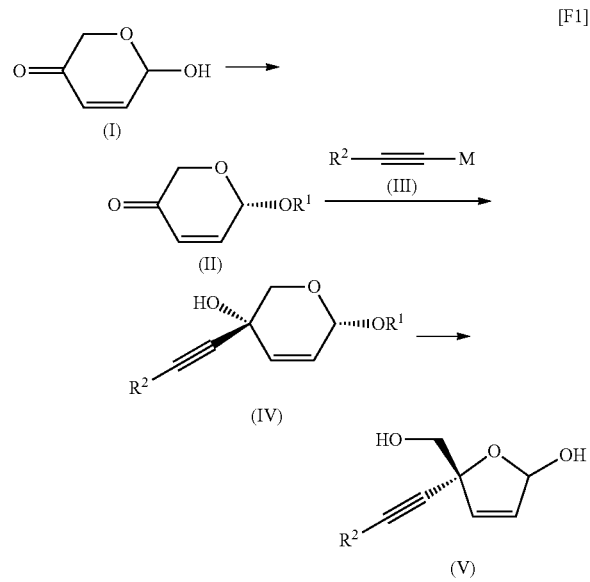

10 Claims, No Drawings

METHOD FOR PRODUCING ACYLOXYPYRANONE COMPOUND, METHOD FOR PRODUCING ALKYNE COMPOUND, AND METHOD FOR PRODUCING DIHYDROFURAN COMPOUND

This application is the National Phase of PCT International Application No. PCT/JP2011/058835, filed on Apr. 7, 2011, which claims priority under 35 U.S.C. 119(a), to Patent Application No. 2010-088819, filed in JAPAN on Apr. 7, 2010, all of which are hereby expressly incorporated by reference into the present application.

TECHNICAL FIELD

The present invention relates to a method for producing an acyloxypyranone compound, to a method for producing an alkyne compound, and to a method far producing a dihydrofuran compound. More particularly, the invention relates to a method for producing an intermediate of 4'-ethynyl-2',3'-didehydro-3'-deoxythymidine (4'-ethynyl d4T) from 6-hydroxy-2H-pyran-3(6H)-one (hydroxypyranone) serving as a starting material.

BACKGROUND ART

4'-Ethynyl-2',3'-didehydro-3'-deoxythymidine (hereinafter referred to as 4'-ethynyl d4T) is a compound which is a promising ingredient of a drug for acquired immune deficiency syndrome (AIDS) (see, for example, Patent Documents 1 and 2). However, conventional methods for synthesizing 4'-ethynyl d4T (see Patent Document 1 and Non-Patent Document 1) require a large number of synthesis steps, making these methods high-cost and unsuitable for mass production, which is problematic.

Meanwhile, another method for producing 4'-ethynyl d4T is disclosed. The disclosed method employs furfuryl alcohol or levo-glucocenone as a starting material and requires a relatively small number of steps (see, for example, Patent Document 2). However, the problem involved in the production method; i.e., high production cost, cannot be completely solved, for the following reasons.

1) Patent Document 2 discloses kinetic optical resolution of acetyloxypyranone by use of a hydrolase. In this process, only one enantiomer of an acetyloxypyranone racemate is selectively removed via hydrolysis. Therefore, the maximum yield is limited to 50%. Meanwhile, synthesis of an optically active acetyloxypyranone from a hydroxypyranone as a raw material is also disclosed. In this synthesis, an optically active acetyloxypyranone is synthesized through dynamic kinetic optical resolution, while racemization proceeds in the reaction system (see, for example, Non-Patent Document 2). In this case, the production yield can reach 100%. However, the reaction for producing a desired enantiomer which reaction employs a lipase (*Candida cylindracea* or *Candida rugosa*) proceeds at a very low rate of reaction. In addition, there is a phrase "poor reproducibility due to an unknown reason" in Non-Patent Document 2. Thus, the production method is not considered a method suitable for mass production.

2) Patent Document 2 discloses a method for synthesizing an alkyne compound including causing an acetylene organic metal compound to act on an acetyloxypyranone. In this method, not only an alkyne compound having an acetylene moiety at the trans position to the acetyl group, but also a large amount of a diastereomer thereof having an acetylene moiety at the cis position are yielded. The diastereomer provides an enantiomer of 4'-ethynyl d4T instead of the target 4'-ethynyl d4T. Notably, Patent Document 2 does not disclose the ratio of formed alkyne compound to formed diastereomer.

3) Patent Document 2 discloses a method for synthesizing a dihydrofuran compound including causing a hydrolase to act on an alkyne compound. Although the disclosed step attains a crude product yield of about 90%, the net yield is lower, since the crude product contains reaction by-products, a diastereomer, and reaction residues.

Therefore, there is still keen demand for a low-cost method for mass-producing 4'-ethynyl d4T and a dihydrofuran compound, which is an intermediate thereof.

PRIOR ART DOCUMENTS

Patent Documents

Patent Document 1: Japanese Patent Application Laid-Open (kokai) No. 2006-528972
Patent Document 2: WO 2009/084655, pamphlet

Non-Patent Documents

Non-Patent Document 1: Maddaford, et al., Synthesis, 2007, No. 9, p. 1378-1384
Non-Patent Document 2: Tetrahedron Letters, Vol. 38, p. 1655, 1997

SUMMARY OF THE INVENTION

Problems to be Solved by the Invention

Thus, an object to be attained by the present invention is to provide a method for producing an acyloxypyranone compound, a method for producing an alkyne compound, and a method for producing a dihydrofuran compound, these methods being provided for producing 4'-ethynyl d4T in a more simple manner, at low cost, and on a large scale.

Means for Solving the Problems

The present inventors have conducted extensive studies in order to attain the aforementioned object, and have found that the object can be attained by a method for producing 4'-ethynyl d4T from a hydroxypyranone serving as a starting material via a specific intermediate compound (i.e., a compound represented by the below-mentioned formula (V)). The present invention has been accomplished on the basis of this finding.

Accordingly, the present invention provides the following.
(1) A method for producing an acyloxypyranone compound represented by the following formula (II):

[F2]

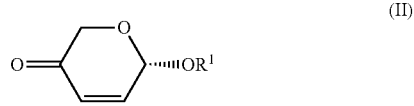

(II)

(wherein R[1] represents an acyl group), characterized in that the method comprises causing to act on a hydroxypyranone represented by the following formula (I):

[F1]

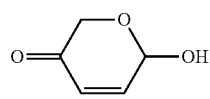
(I)

an acylating agent and a hydrolase in a water-containing organic solvent.

(2) A method for producing an alkyne compound represented by the following formula (IV):

[F4]

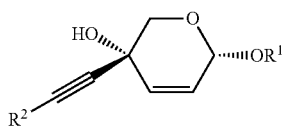
(IV)

(wherein R[1] represents an acyl group, and R[2] represents a hydrogen atom or a tri-substituted silyl group), characterized in that the method comprises causing an acetylene organic metal compound represented by the following formula (III):

[F3]

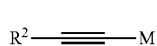
(III)

(wherein R[2] represents a hydrogen atom or a tri-substituted silyl group, and M represents an alkali metal atom, aluminum, or a magnesium monohalide) and a coordinating additive to act on the acyloxypyranone compound represented by formula (II) produced through a production method as recited in (1) above.

(3) A method for producing a dihydrofuran compound represented by the following formula (V):

[F5]

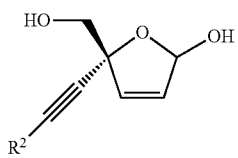
(V)

(wherein R[2] has the same meaning as defined in formula (IV)), characterized in that the method comprises hydrolyzing, in the presence of an acid or a hydrolase, the alkyne compound represented by formula (IV) produced through a production method as recited in (2) above.

(4) A method for producing an alkyne compound represented by the following formula (IV):

[F8]

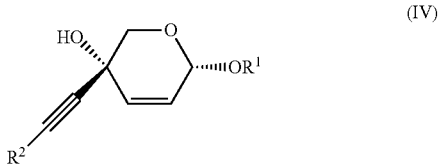
(IV)

(wherein R[1] represents an acyl group, and R[2] represents a hydrogen atom or a tri-substituted silyl group), characterized in that the method comprises causing an acetylene organic metal compound represented by the following formula (III):

[F7]

(III)

(wherein R[2] represents a hydrogen atom or a tri-substituted silyl group, and M represents an alkali metal atom, aluminum, or a magnesium monohalide) and a coordinating additive to act on an acyloxypyranone compound represented by the following formula (II):

[F6]

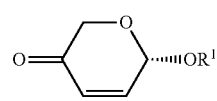
(II)

(wherein R[1] represents an acyl group).

(5) A method for producing a dihydrofuran compound represented by the following formula (V):

[F10]

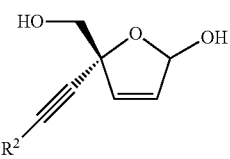
(V)

(wherein R[2] represents a hydrogen atom or a tri-substituted silyl group), characterized in that the method comprises hydrolyzing, in the presence of an acid or a hydrolase, the alkyne compound represented by the following formula (IV):

[F9]

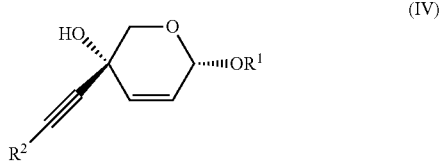

(IV)

(wherein $R^1$ represents an acyl group, and $R^2$ has the same meaning as defined in formula (V)).

(6) A method for producing an acyloxypyranone compound as described in (1) above, wherein the acyl group of $R^1$ is a benzoyl group, and the acylating agent is benzoic acid, benzoic anhydride, or a benzoic acid ester.

(7) A method for producing an alkyne compound as described in (2) above, wherein the coordinating additive is an amine compound.

(8) A method for producing an acyloxypyranone compound as described in (1) above, wherein the hydrolase is a lipase derived from *Candida rugosa*.

(9) A method for producing an acyloxypyranone compound as described in (1) above, wherein the water-containing organic solvent has a water content of 100 ppm to 8,000 ppm.

Effects of the Invention

According to the present invention, an acyloxypyranone compound, an alkyne compound, and a dihydrofuran compound, which are intermediates of 4'-ethynyl d4T, can be produced in a more simple manner, at low cost, and on a large scale, whereby 4'-ethynyl d4T can be produced in a more simple manner, at low cost, and on a large scale, as compared with currently employed processes. Since the compound 4'-ethynyl d4T is a candidate active ingredient of an effective drug for the treatment of HIV infection, the production methods of the present invention are very useful for attaining the treatment in practice by use of the drug.

MODES FOR CARRYING OUT THE INVENTION

The present invention will next be described in detail. However, the following detailed description should not be construed as limiting the invention thereto. Other than the following embodiments, the present invention may be carried out with appropriate modification, so long as the gist of the present invention is not impaired. Also, all the publications referred to in this specification, including prior art documents, Laid-Open patent applications, patent publications, and other patent documents are incorporated herein by reference.

1. Synthesis of an Acyloxypyranone Compound Represented by Formula (II)

The acyloxypyranone compound represented by formula (II) can be produced by causing an acylating agent and a hydrolase to act on the hydroxypyranone represented by formula (I) in a water-containing organic solvent.

The hydroxypyranone represented by formula (I) serving as a raw material may be synthesized from furfuryl alcohol by two steps through a method disclosed in, for example, Tetrahedron Vol. 56, p. 8953, 2000.

The reaction is performed in the state in which the hydroxypyranone is dissolved or dispersed in an organic solvent.

In the reaction system, racemization of the hydroxypyranone proceeds in parallel. Therefore, either a racemate or an enantiomer of the hydroxypyranone may be used as a raw material. Theoretically, the yield of the acyloxypyranone compound product may be in excess of 50%.

Examples of the organic solvent which may be used in the reaction include alkanes such as hexane and heptane; cycloalkanes such as cyclohexane; ethers such as diethyl ether, tetrahydrofuran, and diisopropyl ether; aromatics such as benzene and toluene; esters such as ethyl acetate, butyl acetate, vinyl acetate, and vinyl benzoate; ketones such as acetone and methyl isobutyl ketone; and haloalkanes such as methylene chloride. From the viewpoints of rate of reaction and optical selectivity, aromatics, ethers, alkanes, haloalkanes, and esters are preferred, with toluene, diisopropyl ether, cyclohexane, methylene chloride, and vinyl acetate being particularly preferred.

When an organic solvent having an appropriate water content is used, the rate and reproducibility of the reaction can be drastically enhanced. The water content of the organic solvent is preferably 100 ppm to 8,000 ppm, more preferably 190 ppm to 4,000 ppm. When the water content is excessively low, a sufficient effect fails to be attained, which is not preferred. From the viewpoints of prevention of decrease in reactivity and prevention of reverse reaction, the water content is preferably 8,000 ppm or less. For preparing an organic solvent having an appropriate water content, an appropriate amount of water may be added to a commercial solvent. In a more simple manner, an excess amount of water is added to a commercial solvent, and the mixture is sufficiently stirred. Then, the mixture is allowed to stand for phase separation, and the aqueous layer is removed.

Examples of the acylating agent which may be employed in the reaction include acid anhydrides such as acetic anhydride, propionic anhydride, butyric anhydride, isobutyric anhydride, pivalic anhydride, hexanoic anhydride, heptanoic anhydride, and benzoic anhydride; vinyl esters such as vinyl acetate, vinyl butyrate, vinyl pivalate, and vinyl benzoate; alkyl esters such as ethyl acetate, butyl acetate, isopropyl acetate, ethyl isobutyrate, and ethyl benzoate; and carboxylic acids such as acetic acid, propionic acid, butyric acid, isobutyric acid, pivalic acid, hexanoic acid, heptanoic acid, and benzoic acid. Among them, acid anhydrides and vinyl esters are preferred, with acetic anhydride, vinyl acetate, benzoic anhydride, vinyl benzoate, and vinyl pivalate being more preferred. Thus, specific examples of the acyl group $R^1$ of the present invention include acryl groups derived from the acylating agent; i.e., acetyl, ethylcarbonyl, n-propylcarbonyl, isoproylcarbonyl, t-butylcarbonyl, n-pentylcarbonyl, n-hexylcarbonyl, and benzoyl. Generally, the minimum required amount of the acylating agent used in the reaction is 1 eq. by mole or more, with respect to 1 eq. by mole of hydroxypyranone serving as a substrate. In the case of an oily compound such as a vinyl ester, the compound may be used as a solvent in a large amount.

The hydrolase used in the reaction may be any enzyme, so long as the enzyme provide an acyloxypyranone compound represented by formula (II) of a desired stereochemistry; i.e., the (R) form. Among such enzymes, a lipase derived from *Candida cylindracea* or a lipase derived from *Candida rugosa* may preferably be used. The lipase used in the reaction may be a purified enzyme or an enzyme preparation containing an appropriate diluent (e.g., lactose). In use, the enzyme may be immobilized by an appropriate carrier. The amount of hydrolase used in the reaction may be 10 parts by weight to 0.01 parts by weight, with respect to 100 parts by weight of hydroxypyranone. From the viewpoint of cost and rate of reaction, the amount of hydrolase is more preferably 5 parts by weight to 0.5 parts by weight. In a more preferred mode, the hydrolase is used after absorption of moisture. In one procedure of moisture absorption, a hydrolase is allowed to stand in air having a humidity of 50% to 80% for about 12 hours.

The reaction may be accelerated by adding a base serving as an additive to the reaction system. Examples of the base which may be employed in the reaction include alkylamines such as diisopropylamine and triethylamine; and pyridines such as pyridine and 2,6-lutidine. The amount of the base used in the reaction is 0.01 eq. by mole to 10 eq. by mole, with respect to 100 eq. by mole of hydroxypyranone, more preferably 0.1 eq. by mole to 1 eq. by mole.

The reaction temperature is preferably 0° C. to 50° C., more preferably 20° C. to 40° C.

After completion of reaction, extraction of the organic layer, washing, concentration (concentration under reduced pressure), and purification (purification with a column, filtration through silica gel, recrystallization, etc.) are performed through known techniques, whereby an (R) enantiomer of the acyloxypyranone compound; i.e., the acyloxypyranone compound represented by formula (II) can be preferentially produced at an enantiomeric excess of 75% or higher, or 90% or higher. Through employment of the above production procedure, a very high rate of reaction can be attained.

2. Synthesis of an Alkyne Compound Represented by Formula (IV)

The alkyne compound represented by formula (IV) can be produced by causing an acetylene organic metal compound represented by formula (III) and a coordinating additive to act on the acyloxypyranone compound represented by formula (II).

The acetylene organic metal compound represented by formula (III) may be prepared by use of a tri-substituted silylacetylene (e.g., trimethylsilylacetylene, triethylsilylacetylene, t-butyldimethylsilylacetylene, or triphenylsilylacetylene) and a base.

Examples of the tri-substituted silyl group of the present invention include tri-substituted silyl groups each having three substituents selected from C1 to C4 alkyl groups and a phenyl group, wherein the three substituents may be identical to or different from one another. Specific examples include trimethylsilyl, triethylsilyl, t-butyldimethylsilyl, and triphenylsilyl.

Examples of the base include alkylmetals such as n-butyllithium; metal hydrides such as sodium hydride; alkoxymetals such as tert-butyloxypotassium; metal amides such as lithium hexamethyldisilazide and lithium diisopropylamide. Notably, the alkali metal forming the base serves as M in the acetylene organic metal compound represented by formula (III). Use of a metal amide as a base is more preferred, since the ammonium anion serves as a coordinating additive, thereby requiring no addition of a coordinating additive.

The coordinating additive may be any coordinating additive, so long as it can coordinate to the ion of the alkali metal atom M (e.g., Li ion) forming the acetylene organic metal compound represented by formula (III). Examples of the coordinating additive include ethers such as dimethoxyethane; alkylamine compounds such as diisopropylamine, triethylamine, triphenylamine, and diisopropylethylamine; silylamine compounds such as bis(trimethylsilyl)amine; arylamine compounds such as triphenylamine; alkyldiamine compounds such as ethylenediamine and tetramethylethylenediamine; cyclic amine compounds such as quinuclidine and hexamethylenetetramine; and hexamethylphosphoric triamide. Through combined action of the coordinating additive and the acetylene organic metal compound in the reaction, the selectivity of attacking the acetylene organic metal compound to the acyloxypyranone compound can be drastically enhanced, whereby the alkyne compound yield can be increased.

The reaction temperature is preferably −80° C. to 50° C., more preferably −70° C. to 10° C.

After completion of reaction, extraction of the organic layer, washing, concentration (concentration under reduced pressure), and purification (purification with a column, filtration through silica gel, recrystallization, etc.) are performed through known techniques.

Through employment of the production procedure, an alkyne compound of a desired stereochemistry; i.e., the alkyne compound represented by formula (IV) can be produced considerably preferentially to a diastereomer thereof.

3. Synthesis of a Dihydrofuran Compound Represented by Formula (V)

The dihydrofuran compound represented by formula (V) can be synthesized by hydrolyzing the alkyne compound represented by formula (IV) in a solvent by the action of an acid and water or the action of a hydrolase and water.

Preferably, the reaction is performed under solvent-diluted conditions for smoothly performing the reaction including sufficient mixing and dispersing the reagents used in the reaction. No particular limitation is imposed on the solvent employed in the reaction, so long as the solvent is inert to the reaction. Examples of the solvent include ethers such as diethyl ether, methyl t-butyl ether, tetrahydrofuran, diethyl ether, dimethoxymethane, diethoxymethane, ethylene glycol dimethyl ether, ethylene glycol diethyl ether, ethylene glycol dibutyl ether, diethylene glycol dimethyl ether, diethylene glycol diethyl ether, diethylene glycol dibutyl ether, triethylene glycol dimethyl ether, 1,4-dioxane, and anisole; ketones such as acetone, methyl ethyl ketone, diethyl ketone, 2-pentanone, methyl isobutyl ketone, and cyclohexanone; aliphatic hydrocarbons such as pentane, hexane, cyclohexane, methylcyclohexane, heptane, octane, and decane; halohydrocarbons such as chloroform, tetrachlorocarbon, dichloroethane, and tetrachloroethylene; aromatic hydrocarbons such as benzene, toluene, xylene, chlorobenzene, o-dichlorobenzene, m-dichlorobenzene, p-dichlorobenzene, nitrobenzene, and tetrahydronaphthalene; nitriles such as acetonitrile and propionitrile; esters such as methyl acetate, ethyl acetate, butyl acetate, and ethyl propionate; amides such as N,N-dimethylformamide, N,N-dimethylacetamide, and N-methylpyrrolidone; ureas such as 1,3-dimethylimidazolidinone and N,N,N',N'-tetramethylurea; and pyridines such as pyridine, 2-picoline, 3-picoline, 4-picoline, and 5-ethyl-2-picoline. These solvents may be used singly or in combination.

Water is preferably used in an amount of 100 to 0.1 parts by weight with respect to 100 parts by weight of the alkyne compound, more preferably 10 to 0.5 parts by weight.

Examples of the acid which may be used include hydrochloric acid, sulfuric acid, trichloroacetic acid, trifluoroacetic acid, and methanesulfonic acid.

Any hydrolase such as lipase, esterase, protease, or glycosidase may be used, and so long as the enzyme can hydrolyze the target alkyne compound. Among them, lipase is preferably used, with lipases derived from *Burkholderia cepacia*, *Candida cylindracea*, and *Candida rugosa* being more preferably used. The lipase may be a purified enzyme or an enzyme preparation containing an appropriate diluent (e.g., lactose). In use, the enzyme may be immobilized by an appropriate carrier. The amount of hydrolase used in the reaction may be 10 parts by weight to 0.01 parts by weight, with respect to 100 parts by weight of the alkyne compound.

From the viewpoint of cost and rate of reaction, the amount of hydrolase is more preferably 1 part by weight to 0.1 parts by weight.

As described above, an intermediate of 4'-ethynyl d4T can be produced from 6-hydroxy-2H-pyran-3(6H)-one (i.e., a hydroxypyranone represented by formula (I)) serving as a starting material through the following reaction scheme.

[F11]

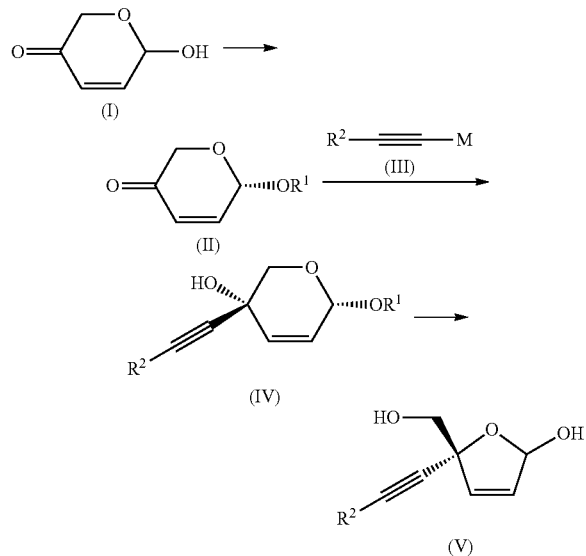

By use of the dihydrofuran compound synthesized according to the present invention, 4'-ethynyl d4T may be synthesized through a known method; e.g., a method disclosed in WO 2009/084655 (pamphlet). An acyloxypyranone compound, an alkyne compound, and a dihydrofuran compound can be mass-produced in a more simple manner at lower cost, as compared with conventional methods. Thus, 4'-ethynyl d4T can be mass-produced from these compounds, in a simple manner at low cost.

EXAMPLES

The present invention will next be described in more detail by way of examples, which should not be construed as limiting the invention thereto.

$^1$H-NMR and LC were measured by means of the following apparatuses under the following conditions (NMR: nuclear magnetic resonance spectrometry, LC; liquid chromatography).

[1] $^1$H-NMR
Apparatus: JNM-ECP300 (product of JEOL) (300 MHz)
Solvent: $CDCl_3$

[2] LC
Exemplary LC measurement conditions 1: Percent conversion, quantitation, and analytical conditions in determination of target/target diastereomer ratio of (2R,5R)-2-acyloxy-5,6-dihydro-2H-pyrano-5-((trimethylsilyl)ethynyl)-5-ol
LC: Agilent 1100
Column: Capcellpak C18 MGII 4.6×100 mm 3 μm
Oven Temp: 40° C.
Eluent: $CH_3CN$, $H_2O$
$CH_3CN$=20% (0 min)→80% (15 min)→80% (10 min)
Flow rate: 1.2 mL/min
Detector: UV 195 nm Exemplary LC measurement conditions 2: Analytical conditions in determination of optical purity of (R)-2-acyloxy-5,6-dihydro-2H-pyrano-5-one
LC: Shimadzu Corporation, LC-10A
Column: Capcellpak C18 MGII 4.6×100 mm 3 μm+Chiralpak AD-RH 4.6×150 mm
Oven Temp: 40° C.
Eluent: $CH_3CN$, $H_2O$
$CH_3CN$=10% (0 min)→80% (20 min)→80% (10 min)
Flow rate: 1.0 mL/min
Detector: UV 195 nm The yield of a product was determined through quantitation by HPLC with a calibration curve drawn in advance. In the case of determination of the yield of an acyloxypyranone compound, three solutions of acyloxypyranone compound in acetonitrile having different concentrations were prepared, and a predetermined amount of t-butylbenzene (internal standard) was added to each solution. The thus-prepared samples were analyzed through HPLC, and a calibration curve was drawn from area ratios (acyloxypyranone compound:internal standard). Then, an aliquot was sampled from an acyloxypyranone compound solution of an unknown concentration (i.e., analyte), and a predetermined amount of the internal standard was added to the sampled aliquot. The mixture was analyzed through HPLC, and an area ratio (acyloxypyranone compound:internal standard). The acyloxypyranone solution concentration was determined by the calibration curve, to thereby determine the product yield.

Example 1

To a nitrogen-substituted reactor, 6-hydroxy-2H-pyran-3(6H)-one (i.e., a hydroxypyranone represented by formula (I)) (565 g) and a solution of benzoic anhydride (2,334 g) in toluene (total weight: 15,545 g) were added, and the mixture was concentrated under reduced pressure. Toluene was further added to the concentrated product, to thereby adjust the water content of the toluene solution to 183 ppm. To the reactor, water (22.58 g) and lipase MY-30 (enzyme derived from *Candida rugosa*, commercial product of Meito Sangyo Co., Ltd.) (1,680 g) were added, and the mixture was stirred at 30° C. The extent of reaction was monitored through high-performance liquid chromatography. After completion of reaction, the solid matter was filtered off, and the filtrate was washed with 10% aqueous potassium bicarbonate and water, followed by concentration under reduced pressure. Subsequently, toluene (252 g), ethanol (928 g), and heptane (5,569 g) were added to the concentrate, to thereby perform crystallization, and the crystals were recovered through filtration at −5° C., to thereby yield 902 g of (R)-2-benzoyloxy-5,6-dihydro-2H-pyran-5-one represented by formula (II) as crystals. The crystals were dissolved in methylene chloride (5,575 g), and the solution was analyzed. The enantiomeric excess and yield were found to be 99.9% and 76.2%, respectively. The $^1$H-NMR data of the compound are as follows:

$^1$H-NMR: δH (300 MHz; $CDCl_3$) 8.04 (d, 2H), 7.60 (t, 1H), 7.45 (t, 2H), 7.02 (dd, 1H), 6.73 (d, 1H), 6.32 (d, 1H), 4.59 (d, 1H), and 4.27 (d, 1H).

Example 2

To a nitrogen-substituted reactor, methylene chloride (6,164 g) and trimethylsilylacetylene (446 g) were added, and the mixture was cooled to −60° C. To the mixture, a solution of n-butyllithium in hexane (1.65 mol/L) (2,626 L) and tetramethylethylenediamine (539 g) were added dropwide. Subsequently, a solution of (R)-2-benzoyloxy-5,6-dihydro-2H- pyran-5-one (822 g) produced through the same method as employed in Example 1 in methylene chloride (total weight: 6,477 g) was added dropwise thereto. The extent of reaction was monitored through high-performance liquid chromatography. After completion of reaction, the reaction was quenched with a mixture of acetic acid and methylene chloride (1,644 g) and water (5,752 g), and the organic layer was separated. The organic layer was washed with 10% aqueous potassium bicarbonate and water, followed by concentration under reduced pressure. Quantitation of the crude product through high-performance liquid chromatography revealed that the product contained 1,013 g of (2R,5R)-2-benzoyloxy-5,6-dihydro-2H-pyrano-5-((trimethylsilyl)ethynyl)-5-ol represented by formula (IV) (yield: 84.9%). The stereoisomer ratio (target/target diastereomer ratio) of the obtained (2R, 5R)-2-benzoyloxy-5,6-dihydro-2H-pyrano-5-((trimethylsilyl)ethynyl)-5-ol was 229/10.

Example 3

To a nitrogen-substituted reactor, lipase MY-30 (253 g), disodium hydrogenphosphate (80 g), sodium dihydrogenphosphate (68 g), and water (5.27 kg) were added, and the mixture was stirred at 25° C. To the mixture, a solution of (2R,5R)-2-benzoyloxy-5,6-dihydro-2H-pyrano-5-((trimethylsilyl)ethynyl)-5-ol (1,013 g) produced through the same method as employed in Example 2 in t-butyl methyl ether (total weight 9,384 g) was added. The extent of reaction was monitored through high-performance liquid chromatography. After completion of reaction, the reaction mixture was filtered, and the organic layer was separated. The organic layer was washed with 10% aqueous potassium bicarbonate and water, followed by concentration under reduced pressure. Quantitation of the crude product through high-performance liquid chromatography revealed that the product contained 620 g of (5R)-2,5-dihydro-5-hydroxymethyl-5-((trimethylsilyl)ethynyl)furan-2-ol represented by formula (V) (yield: 91.9%).

As is clear from Examples 1 to 3, the production method was found to provide a target product at particularly high optical purity in a large amount.

Synthesis of (R)-2-acyloxy-5,6-dihydro-2,4-pyran-5-one, an acyloxypyranone compound represented by formula (II)

Examples 4 to 11

In each Example, 6-hydroxy-2H-pyran-3(6H)-one (i.e., a hydroxypyranone represented by formula (I)) was added to a reactor in an amount specified in Table 1. A solvent having high water content was added in an amount (parts by weight) specified in Table 1, with respect to 1 part by mass of hydroxypyranone, and the mixture was maintained at 30° C. Then, an acylating agent specified in Table 1 was added in an amount of 4 eq. by mole, with respect to 1 eq. by mole of hydroxypyranone, and lipase MY-30 (enzyme derived from *Candida rugosa*, commercial product of Meito Sangyo Co., Ltd.) was added in an amount of 2 parts by weight, with respect to 1 part by weight of hydroxypyranone. The resultant mixture was stirred. The extent of reaction was monitored through high-performance liquid chromatography. After completion of reaction, the lipase was removed through filtration under reduced pressure, and the filtrate was concentrated under reduced pressure. The residue was purified through silica gel chromatography, to thereby yield (R)-2-acyloxy-5,6-dihydro-2H-pyran-5-one. The percent conversion to ((R)-2-acyloxy-5,6-dihydro-2H-pyran-5-one, the time required for reaching the percent conversion (value in parentheses in Table 1), the yield, and the optical purity are shown in Table 1. Table 1 also shows the water content of each solvent (value in parentheses). The optical purity was determined through high-performance liquid chromatography by use of a chiral column.

In Examples 4 to 8, (R)-2-benzoyloxy-5,6-dihydro-2H-pyran-5-one was produced. The $^1$H-NMR data of the compound are as follows:
$^1$H-NMR: δH (300 MHz; CDCl$_3$) 8.04 (d, 2H), 7.60 (t, 1H), 7.45 (t, 2H), 7.02 (dd, 1H), 6.73 (d, 1H), 6.32 (d, 1H), 4.59 (d, 1H), and 4.27 (d, 1H).

In Example 9, (R)-2-acetyloxy-5,6-dihydro-2H-pyran-5-one was produced. The $^1$H-NMR data of the compound are as follows:
$^1$H-NMR: δH (300 MHz; CDCl$_3$) 6.89 (dd, 1H), 6.46 (d, 1H), 6.24 (d, 1H), 4.49 (d, 1H), 4.20 (d, 1H), and 2.11 (s, 3H).

In Example 10, (R)-2-isopropylcarbonyloxy-5,6-dihydro-2H-pyran-5-one was produced. The $^1$H-NMR data of the compound are as follows:
$^1$H-NMR: δH (300 MHz; CDCl$_3$) 6.90 (dd, 1H), 6.49 (dd, 1H), 6.24 (d, 1H), 4.48 (d, 1H), 4.20 (d, 1H), 2.63 (m, 1H), and 1.20 (m, 6H).

In Example 11, (R)-2-n-pentylcarbonyloxy-5,6-dihydro-2H-pyran-5-one. The $^1$H-NMR data of the compound are as follows:
$^1$H-NMR: δH (300 MHz; CDCl$_3$) 6.90 (dd, 1H), 6.49 (dd, 1H), 6.24 (d, 1H), 4.48 (d, 1H), 4.20 (d, 1H), 2.35 (m, 2H), 1.63 (m, 2H), 1.30 (m, 4H), and 0.85 (m, 3H).

Comparative Examples 1 to 3

In each case, 6-hydroxy-2H-pyran-3(6H)-one (i.e., hydroxypyranone) was added to a reactor in an amount specified in Table 1. A solvent having low water content was added in an amount (parts by weight) specified in Table 1, with respect to 1 part by mass of hydroxypyranone, and the mixture was maintained at 30° C. Then, an acylating agent specified in Table 1 was added in an amount (eq. by mole) in Table 1, with respect to 1 eq. by mole of hydroxypyranone, and a lipase specified in Table 1 was added in an amount of 1 part by weight, with respect to 1 part by weight of hydroxypyranone. The resultant mixture was stirred. The extent of reaction was monitored through high-performance liquid chromatography. After completion of reaction, the lipase was removed through filtration under reduced pressure, and the filtrate was concentrated under reduced pressure. The residue was purified through silica gel chromatography, to thereby yield (R)-2-benzoyloxy-5,6-dihydro-2H-pyran-5-one. The percent conversion to ((R)-2-acyloxy-5,6-dihydro-2H-pyran-5-one, the time required for reaching the percent conversion (value in parentheses in Table 1), the yield, and the optical purity are shown in Table 1. Table 1 also shows the water content of each solvent (value in parentheses). The optical purity was determined through high-performance liquid chromatography by use of a chiral column.

Comparative Examples 4 to 8

In each case, 6-hydroxy-2H-pyran-3(6H)-one (i.e., hydroxypyranone) was added to a reactor in an amount specified in Table 2. A solvent having high water content was added in an amount (parts by weight) specified in Table 2, with respect to 1 part by mass of hydroxypyranone, and the mixture was maintained at 30° C. Then, vinyl acetate serving as an acylating agent was added in a solvent amount, and a selected lipase was added in an amount of 1 part by weight, with respect to 1 part by weight of hydroxypyranone. The resultant mixture was stirred. The extent of reaction was monitored through high-performance liquid chromatography. After completion of reaction, the lipase was removed through filtration under reduced pressure, and the filtrate was concentrated under reduced pressure. The residue was purified through silica gel chromatography, to thereby yield 2-acetyloxy-5,6-dihydro-2H-pyran-5-one. The percent conversion to (R)-2-acyloxy-5,6-dihydro-2H-pyran-5-one, the time required for reaching the percent conversion (value in parentheses in Table 2), and the optical purity are shown in Table 2. Table 2 also shows the water content of each solvent (value in parentheses). The optical purity was determined through high-performance liquid chromatography by use of a chiral column.

TABLE 1

| | Hydroxy-pyranone | Solvent (water content) | Acylating agent | Enzyme | Conversion | Yield | optical purity (e.e.) |
|---|---|---|---|---|---|---|---|
| Ex. 4 | 100 mg | Toluene (400 ppm) 50 parts by wt. | Benzoic anhydride (4 mole eq.) | Lipase MY-30 | 67% (6.5 hr) | — | 93% |
| Ex. 5 | 5 g | Toluene (400 ppm) 50 parts | Benzoic anhydride (4 mole eq.) | Lipase MY-30 | 97% (3 hr) | 85% | 94% |
| Ex. 6 | 45 g | Toluene (400 ppm) 50 parts | Benzoic anhydride (4 mole eq.) | Lipase MY-30 | 100% (24 hr) | 90% | 94% |
| Ex. 7 | 100 mg | Dichloromethane (aq. satd.) 50 parts | Benzoic anhydride (4 mole eq.) | Lipase MY-30 | 72% (6.5 hr) | — | 94% |
| Ex. 8 | 100 mg | Toluene (400 ppm) 50 parts | Vinyl benzoate (4 mole eq.) | Lipase MY-30 | 93% (6.5 hr) | — | 90% |
| Ex. 9 | 10 mg | Vinyl acetate (260 ppm) 200 parts | Vinyl acetate (solvent amount) | Lipase OF (derived from *candida rugosa*) | 38% (18 hr) | | 78% |
| Ex. 10 | 10 mg | Cyclohexane (120 ppm) 200 parts | Isobutyric anhydride (4 mole eq.) | Lipase MY-30 | 100% (16 hr) | | 86% |
| Ex. 11 | 10 mg | Cyclohexane (120 ppm) 200 parts | n-Hexanoic anhydride (4 mole eq.) | Lipase MY-30 | 100% (16 hr) | | 90% |
| Comp. Ex. 1 | 100 mg | Toluene (29 ppm) 50 parts | Benzoic anhydride (4 mole eq.) | Lipase MY-30 | 9% (6 hr) | — | 89% |
| Comp. Ex. 2 | 20 g | Toluene (29 ppm) 50 parts | Benzoic anhydride (4 mole eq.) | Lipase MY-30 | 23% (4 hr) | — | 90% |
| Comp. Ex. 3 | 10 mg | Dichloromethane (40 ppm) 200 parts | Benzoic anhydride (4 mole eq.) | Lipase MY-30 | 20% (16 hr) | — | 93% |

TABLE 2

| | Hydroxy-pyranone | Solvent (water content) | Acylating agent | Enzyme | Conversion | optical purity (e.e.) |
|---|---|---|---|---|---|---|
| Comp. Ex. 4 | 10 mg | Vinyl acetate (260 ppm) 200 parts | Vinyl acetate (solvent amount) | Lipase derived from *Candida antarctica* | 22% (18 hr) | −78% |
| Comp. Ex. 5 | 10 mg | Vinyl acetate (260 ppm) 200 parts | Vinyl acetate (solvent amount) | Lipase PS (derived from *Pseudomonas cepacia*) | 97% (18 hr) | −63% |
| Comp. Ex. 6 | 10 mg | Vinyl acetate (260 ppm) 200 parts | Vinyl acetate (solvent amount) | Lipase TL IM (derived from *Thermomyces lanuginosus*) | 33% (18 hr) | 0% |
| Comp. Ex. 7 | 10 mg | Vinyl acetate (260 ppm) 200 parts | Vinyl acetate (solvent amount) | Lipase AK (derived from *Pseudomonas fluorescence*) | 85% (18 hr) | −69% |
| Comp. Ex. 8 | 10 mg | Vinyl acetate (260 ppm) 200 parts | Vinyl acetate (solvent amount) | Lipase QLM (derived from *Alcaligenes*) | 99% (18 hr) | −52% |

In Examples 4 to 8, the rate of reaction was drastically enhanced at satisfactory enantiomeric excess, and the reproducibility thereof was attained also on an increased scale, as compared with Comparative Examples 1 to 3. In Example 9, a (R)-acyloxypyranone compound having a target stereochemistry was produced at high enantiomeric excess, as compared with Comparative Examples 4 to 8. Notably, a negative enantiomeric excess means that an (S)-acyloxypyranone compound, a reverse enantiomer, was produced.

Example 12

6-Hydroxy-2H-pyran-3(6H)-one (i.e., hydroxypyranone) (30 mg), toluene with a saturation amount of water, benzoic anhydride (2 eq. by mole, with respect to 1 eq. by mole of hydroxypyranone), 2,6-lutidine (1 eq. by mole, with respect to 1 eq. by mole of hydroxypyranone), and lipase MY-30 (2 parts by weight, with respect to 1 part by weight of hydroxypyranone) were added to a reactor, and the mixture was maintained at 30° C. under stirring, to thereby yield (R)-2-benzoyloxy-5,6-dihydro-2H-pyrano-5-one. The extent of reaction was monitored through high-performance liquid chromatography. The optical purity was determined through high-performance liquid chromatography by use of a chiral column. As a result, percent conversion after 8 hours and enantiomeric excess were 100% and 90.7%, respectively.

Synthesis of (2R,5R)-2-acyloxy-5,6-dihydro-2H-pyrano-5-((trimethylsilyl)ethynyl)-5-ol, an Alkyne Compound Represented by Formula (IV)

Example 13

To a nitrogen-substituted reactor, tetrahydrofuran (75 mL) and trimethylsilylacetylene (4.1 g) were added, and the mixture was cooled to −55° C. To the mixture, a 1.1 mol/L solution (37.5 mL) of lithium hexamethyldisilazide in tetrahydrofuran was added, and the mixture was stirred for 20 minutes. Subsequently, a solution of (R)-2-benzoyloxy-5,6-dihydro-2H-pyran-5-one (7.5 g) produced through the same method as employed in Example 1 in tetrahydrofuran (75 mL) was added dropwise thereto, and the resultant mixture was stirred at −55° C. for 30 minutes. The stereoisomer ratio (target/target diastereomer ratio) of the reaction mixture, determined through high-performance liquid chromatography, was 89/11. The reaction mixture was further stirred for 30 minutes, and the reaction was terminated by adding thereto 0.1 wt. % aqueous phosphoric acid (50 mL). The reaction mixture was extracted with ethyl acetate (50 mL), and the organic layer was concentrated and purified through silica gel chromatography, to thereby yield 6.0 g of (2R,5R)-2-benzoyloxy-5,6-dihydro-2H-pyrano-5-((trimethylsilyl)ethynyl)-5-ol as a target product (yield: 55%). A diastereomer, (2R,5S)-2-benzoyloxy-5,6-dihydro-2,4-pyrano-5-((trimethylsilyl)ethynyl)-5-ol was not obtained. The $^{1}$H-NMR results of the target compound are as follows:

(2R,5R)-2-benzoyloxy-5,6-dihydro-2H-pyrano-5-((trimethylsilyl)ethynyl)-5-ol $^{1}$H-NMR: δH (300 MHz; CDCl$_{3}$) 8.09 (d, 2H), 7.60 (t, 1H), 7.45 (t, 2H), 6.54 (brs, 1H), 6.17 (d, 1H), 5.93 (dd, 1H), 3.98 (brs, 2H), 2.31 (s, 1H), and 0.20 (brs, 9H)

Example 14

To a nitrogen-substituted reactor, dichloromethane (1 mL) and trimethylsilylacetylene (77 μL) were added, and the mixture was cooled to −55° C. To the mixture, a 1.67 mol/L solution (0.33 mL) of n-butyllithium in hexane and N,N,N',N'-tetramethylethylenediamine (81.7 μL) were added, and the mixture was stirred. Subsequently, a solution of (R)-2-benzoyloxy-5,6-dihydro-2H-pyran-5-one (100 mg) produced through the same method as employed in Example 1 in dichloromethane (1 mL) was added dropwise thereto, and the resultant mixture was stirred at −55° C. for 2 hours. The stereoisomer ratio (target/diastereomer ratio) of the reaction mixture, determined through high-performance liquid chromatography, was 94/6. The reaction was terminated by adding acetic acid (0.3 mL) thereto, to thereby yield (2R,5R)-2-benzoyloxy-5,6-dihydro-2H-pyrano-5-((trimethylsilyl)ethynyl)-5-ol as a target product (yield: 80.4% by quantitation).

Example 15

To a nitrogen-substituted reactor, dichloromethane (1 mL) and trimethylsilylacetylene (77 mL) were added, and the mixture was cooled to −55° C. To the mixture, a 1.0 mol/L solution of solution (0.55 mL) of lithium hexamethyldisilazide in hexane was added, and the mixture was stirred. Subsequently, a solution of (R)-2-benzoyloxy-5,6-dihydro-2H-pyran-5-one (100 mg) produced through the same method as employed in Example 1 in dichloromethane (1 mL) was added dropwise thereto, and the resultant mixture was stirred at −55° C. for 2 hours. The stereoisomer ratio (target/diastereomer ratio) of the reaction mixture, determined through high-performance liquid chromatography, was 92/8. The reaction was terminated by adding acetic acid (0.3 mL) thereto, to thereby yield (2R,5R)-2-benzoyloxy-5,6-dihydro-2H-pyrano-5-((trimethylsilyl)ethynyl)-5-ol as a target product (yield: 32.4% by quantitation).

Example 16

To a nitrogen-substituted reactor, 1,2-dimethoxyethane (1 mL) and trimethylsilylacetylene (77 μL) were added, and the mixture was cooled to −55° C. To the mixture, a 1.67 mol/L solution (0.33 mL) of n-butyllithium in hexane was added, and the mixture was stirred. Subsequently, a solution of (R)-2-benzoyloxy-5,6-dihydro-2H-pyran-5-one (100 mg) produced through the same method as employed in Example 1 in 1,2-dimethoxyethane (1 mL) was added dropwise thereto, and the resultant mixture was stirred at −55° C. for 2 hours. The stereoisomer ratio (target/diastereomer ratio) of the reaction mixture, determined through high-performance liquid chromatography, was 86/14. The reaction was terminated by adding acetic acid (0.3 mL) thereto, to thereby yield (2R,5R)-2-benzoyloxy-5,6-dihydro-2H-pyrano-5-((trimethylsilyl)ethynyl)-5-ol as a target product (yield: 75.6% by quantitation).

Example 17

To a nitrogen-substituted reactor, tetrahydrofuran (1 mL) and trimethylsilylacetylene (77 μL) were added, and the mixture was cooled to −55° C. To the mixture, a 1.67 mol/L solution (0.33 mL) of n-butyllithium in hexane and N,N,N',N'-tetramethylethylenediamine (81.7 μL) were added. Subsequently, a solution of (R)-2-benzoyloxy-5,6-dihydro-2H-pyran-5-one (100 mg) produced through the same method as employed in Example 1 in tetrahydrofuran (1 mL) was added dropwise thereto, and the resultant mixture was stirred at −55° C. for 3.5 hours. The stereoisomer ratio (target/diastereomer ratio) of the reaction mixture, determined through high-performance liquid chromatography, was 88/12. The reaction was terminated by adding acetic acid (0.3 mL) thereto, to thereby yield (2R,5R)-2-benzoyloxy-5,6-dihydro-2H-pyrano-5-((trimethylsilyl)ethynyl)-5-ol as a target product (yield: 65.4% by quantitation).

Example 18

To a nitrogen-substituted reactor, dichloromethane (1 mL) and trimethylsilylacetylene (77 μL) were added, and the mixture was cooled to −55° C. To the mixture, a 1.67 mol/L solution (0.33 mL) of n-butyllithium in hexane and triethylamine (0.15 mL) were added, and the mixture was stirred. Subsequently, a solution of (R)-2-benzoyloxy-5,6-dihydro-2H-pyran-5-one (100 mg) produced through the same method as employed in Example 1 in dichloromethane (1 mL) was added dropwise thereto, and the resultant mixture was stirred at −55° C. for 2 hours. The stereoisomer ratio (target/diastereomer ratio) of the reaction mixture, determined through high-performance liquid chromatography, was 91/9. The reaction was terminated by adding acetic acid (0.3 mL) thereto, to thereby yield (2R,5R)-2-benzoyloxy-5,6-dihydro-2H-pyrano-5-((trimethylsilyl))ethynyl)-5-ol as a target product (yield: 46.5% by quantitation).

Example 19

To a nitrogen-substituted reactor, dichloromethane (1 mL) and trimethylsilylacetylene (77 μL) were added, and the mixture was cooled to −55° C. To the mixture, a 1.67 mol/L solution (0.33 mL) of n-butyllithium in hexane and diisopropylethylamine (0.19 mL) were added, and the mixture was stirred. Subsequently, a solution of (R)-2-benzoyloxy-5,6-dihydro-2H)-pyran-5-one (100 mg) produced through the same method as employed in Example 1 in dichloromethane (1 mL) was added dropwise thereto, and the resultant mixture was stirred at −55° C. for 2 hours. The stereoisomer ratio (target/diastereomer ratio) of the reaction mixture, determined through high-performance liquid chromatography, was 92/8. The reaction was terminated by adding acetic acid (0.3 mL) thereto, to thereby yield (2R,5R)-2-benzoyloxy-5,6-dihydro-2H-pyrano-5-((trimethylsilyl)ethynyl)-5-ol as a target product (yield: 42.8% by quantitation).

Example 20

To a nitrogen-substituted reactor, dichloromethane (1 mL) and trimethylsilylacetylene (77 μL) were added, and the mixture was cooled to −55° C. To the mixture, a 1.67 mol/L solution (0.33 mL) of n-butyllithium in hexane and triphenylamine (267 mg) were added, and the mixture was stirred. Subsequently, a solution of (R)-2-benzoyloxy-5,6-dihydro-2H-pyran-5-one (100 mg) produced through the same method as employed in Example 1 in dichloromethane (1 mL) was added dropwise thereto, and the resultant mixture was stirred at −55° C. for 2 hours. The stereoisomer ratio (target/diastereomer ratio) of the reaction mixture, determined through high-performance liquid chromatography, was 92/8. The reaction was terminated by adding acetic acid (0.3 mL) thereto, to thereby yield (2R,5R)-2-benzoyloxy-5,6-dihydro-2H-pyrano-5-((trimethylsilyl)ethynyl)-5-ol as a target product (yield: 55.3% by quantitation).

Example 21

To a nitrogen-substituted reactor, dichloromethane (1 mL) and trimethylsilylacetylene (77 μL) were added, and the mixture was cooled to −55° C. To the mixture, a 1.67 mol/L solution (0.33 mL) of n-butyllithium in hexane and hexamethylphosphoric triamide (94.8 were added, and the mixture was stirred. Subsequently, a solution of (R)-2-benzoyloxy-5, 6-dihydro-2H-pyran-5-one (100 mg) produced through the same method as employed in Example 1 in dichloromethane (1 mL) was added dropwise thereto, and the resultant mixture was stirred at −55° C. for 2 hours. The stereoisomer ratio (target/diastereomer ratio) of the reaction mixture, determined through high-performance liquid chromatography, was 93/7. The reaction was terminated by adding acetic acid (0.3 mL) thereto, to thereby yield (2R,5R)-2-benzoyloxy-5, 6-dihydro-2H-pyrano-5-((trimethylsilyl)ethynyl)-5-ol as a target product (yield: 44.2% by quantitation).

Example 22

To a nitrogen-substituted reactor, dichloromethane (1 mL) and trimethylsilylacetylene (77 μL) were added, and the mixture was cooled to −55° C. To the mixture, a 1.67 mol/L solution (0.33 mL) of n-butyllithium in hexane and hexamethylenetetramine (76.4 mg) were added, and the mixture was stirred. Subsequently, a solution of (R)-2-benzoyloxy-5,6-dihydro-2H-pyran-5-one (100 mg) produced through the same method as employed in Example 1 in dichloromethane (1 mL) was added dropwise thereto, and the resultant mixture was stirred at −55° C. for 2 hours. The stereoisomer ratio (target/diastereomer ratio) of the reaction mixture, determined through high-performance liquid chromatography, was 91/9. The reaction was terminated by adding acetic acid (0.3 mL) thereto, to thereby yield (2R,5R)-2-benzoyloxy-5, 6-dihydro-2H-pyrano-5-((trimethylsilyl)ethynyl)-5-ol as a target product (yield: 58.1% by quantitation).

Comparative Example 9

To a nitrogen-substituted reactor, tetrahydrofuran (4.4 mL) and trimethylsilylacetylene (0.47 g) were added, and the mixture was cooled to −55° C. To the mixture, a 1.56 mol/L solution (3.1 mL) of n-butyllithium in hexane was added, and the mixture was stirred for 20 minutes. Subsequently, solution of (R)-2-acetyloxy-5,6-dihydro-2H-pyran-5-one (0.62 g) produced through the same method as employed in Example 9 in tetrahydrofuran (6 mL) was added dropwise thereto, and the resultant mixture was stirred at −30° C. for 30 minutes. The stereoisomer ratio (target/diastereomer ratio) of the reaction mixture, determined through high-performance liquid chromatography, was 60/15. The reaction mixture was further stirred for 30 minutes, and the reaction was terminated by adding 0.1 wt. % aqueous phosphoric acid (5 mL). The resultant mixture was extracted with ethyl acetate (10 mL), and the organic layer was concentrated and purified through silica gel chromatography, to thereby yield 0.40 g of (2R,5R)-2-acetyloxy-5,6-dihydro-2H-pyrano-5-((trimethylsilyl)ethynyl)-5-ol as a target product (yield: 39%) and 0.04 g of a diastereomer (2R,5S)-2-acetyloxy-5,6-dihydro-2,4-pyrano-5-((trimethylsilyl)ethynyl)-5-ol (yield: 4%).

In Examples 13 to 22, the stereoisomer ratio and the yield of the target product were remarkably high, as compared with Comparative Example 9.

Synthesis of (5R)-2,5-dihydro-5-hydroxymethyl-5-((trimethylsilyl)ethynyl)furan-2-ol, a Dihydrofuran Compound Represented by Formula (V)

Example 23

(2R,5R)-2-Benzoyloxy-5,6-dihydro-2H-pyrano-5-((trimethylsilyl)ethynyl)-5-ol (3.0 g) produced through the same method as employed in Example 2 was added to a nitrogen-substituted reactor and dissolved in a mixture of tetrahydrofuran (30 mL) and water (15 mL). 2N HCl (0.3 g) was added to the mixture, and stirring was performed at 40° C. for 6 hours. Disappearance of raw materials was confirmed through high-performance liquid chromatography and TLC (hexane/ethyl acetate=1/1, detected by potassium permanganate). Then, water (30 mL) and ethyl acetate (30 mL) were added thereto, to thereby partition the mixture. The organic layer was washed sequentially with 5% sodium bicarbonate solution (30 mL) and water (30 mL), concentrated under reduced pressure, and purified through silica gel chromatography, to thereby yield 1.0 g of (5R)-2,5-dihydro-5-hydroxymethyl-5-((trimethylsilyl)ethynyl)furan-2-ol as a target product (yield: 49%). The $^1$H-NMR results of the obtained compound are as follows:

(5R)-2,5-dihydro-5-hydroxymethyl-5-((trimethylsilyl)ethynyl) furan-2-ol $^1$H-NMR: δH (300 MHz; CDCl$_3$) 5.83-6.22 (m, 3H), 3.60-4.25 (m, 2H), and 0.17-0.35 (m, 9H).

Example 24

(2R,5R)-2-Benzoyloxy-5,6-dihydro-2H-pyrano-5-((trimethylsilyl)ethynyl)-5-ol (2.0 g) produced through the same method as employed in Example 2 was added to a nitrogen-substituted reactor and dissolved in acetonitrile (10 mL). Water (8 mL) and then lipase PS-SD (product of Aamano Enzyme Inc.) (0.5 g) were added thereto, and the mixture was stirred at 40° C. for 17 hours. Then, ethyl acetate (20 mL) and water (10 mL) were added thereto, to thereby partition the mixture, and the aqueous layer was removed. The organic layer was washed with 5% sodium bicarbonate solution, concentrated under reduced pressure, and purified through silica gel chromatography, to thereby yield 1.1 g of (5R)-2,5-dihydro-5-hydroxymethyl-5-((trimethylsilyl)ethynyl)furan-2-ol as a target product (yield: 85%).

In Examples 23 and 24, the target product was produced at high yield. Particularly, the yield was more higher in Example 24.

Example 25

To a glass reactor, acetonitrile (300 mL) and (2R,5R)-2-acetyloxy-5,6-dihydro-2H-pyrano-5-((trimethylsilyl)ethynyl)-5-ol produced through the same method as employed in Comparative Example 9 (100 g) were added, and the mixture was heated to 40° C. under stirring. Then, an aqueous solution of lipase PS (10 g) dissolved in water (400 mL) was added dropwise thereto, and the resultant mixture was stirred for 15 hours. The reaction mixture was cooled to 20° C., and water and ethyl acetate were added thereto under stirring, to thereby partition the mixture. The organic layer was concentrated under reduced pressure, and the residue was purified through silica gel column chromatography, to thereby yield 21 g of (5R)-2-hydroxy-5-hydroxymethyl-5-(2-trimethylsilylethynyl)-2,5-dihydrofuran (yield; 25%).

In the above Examples, when R$^1$ is an acetyl group, the target compound was mass-produced in a more simple manner at lower cost, as compared with conventional production. However, the yield was lower than that attained in, for example, Example 3.

Comparative Examples 10 to 22

2-Benzoyloxy-5,6-dihydro-2H-pyrano-5-one racemate (100 mg) was added to a reactor, and tetrahydrofuran (500 mg) and 20 mM phosphate buffer (500 mg) were added thereto. The mixture was maintained at 30° C. To the mixture, a lipase specified in Table 3 was added in an amount by weight, with respect to 1 unit weight of 2-benzoyloxy-5,6-dihydro-2H-pyrano-5-one racemate, and the mixture was stirred for a period of time specified in Table 3. The optical purity was determined through high-performance liquid chromatography by use of a chiral column. Specifically, the area ratio of (R)-2-benzoyloxy-5,6-dihydro-2H-pyrano-5-one to (S)-2-benzoyloxy-5,6-dihydro-2,4-pyrano-5-one was calculated. As a result, when any of the lipases listed in Table 3 was used, the target (R) form was not preferentially yielded.

TABLE 3

| | Enzyme | Amount of enzyme | Time | (R)/(S) area ratio |
|---|---|---|---|---|
| Comp. Ex. 10 | Lipase PS Amano SD | 0.6 wt. units | 18 hr | 50/50 |
| Comp. Ex. 11 | Lipase G Amano50 | 0.3 wt. units | 4 hr | 49/51 |
| Comp. Ex. 12 | Lipase AS Amano | 0.3 wt. units | 18 hr | 53/47 |
| Comp. Ex. 13 | Lipase AK Amano | 0.3 wt. units | 18 hr | 50/50 |
| Comp. Ex. 14 | Lipase AYS Amano | 0.3 wt. units | 18 hr | 12/88 |
| Comp. Ex. 15 | Lipase MY-30 | 0.2 wt. units | 20 hr | 3/97 |
| Comp. Ex. 16 | Lipase QLM | 0.2 wt. units | 20 hr | 50/50 |
| Comp. Ex. 17 | Lipase TL | 0.2 wt. units | 20 hr | 50/50 |
| Comp. Ex. 18 | Lipase PS/C amano II | 0.2 wt. units | 20 hr | 50/50 |
| Comp. Ex. 19 | Lipase acrylic resin from *Candida antarctica* | 0.2 wt. units | 3 hr | 50/50 |
| Comp. Ex. 20 | Lipase PL | 0.2 wt. units | 3 hr | 50/50 |
| Comp. Ex. 21 | Lipase SL | 0.2 wt. units | 3.5 hr | 50/50 |
| Comp. Ex. 22 | TOYOBO Immobilized lipase | 0.2 wt. units | 4 hr | 50/50 |

INDUSTRIAL APPLICABILITY

According to the method of the present invention, an acyloxypyranone compound, an alkyne compound, and a dihydrofuran compound, which are intermediates of 4'-ethynyl d4T, can be produced in a more simple manner, at low cost, and on a large scale, as compared with conventional methods, whereby 4'-ethynyl d4T can be produced from these compounds in a more simple manner, at low cost, and on a large scale. Since the compound 4'-ethynyl d4T is a candidate active ingredient of an effective drug for the treatment of HIV infections, the production methods of the present invention are very useful for attaining the treatment in practice by use of the drug.

The invention claimed is:

1. A method for producing an acyloxypyranone compound represented by the following formula (II):

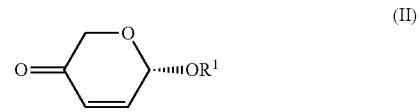

wherein R¹ represents an acyl group, comprising:
reacting a hydroxypyranone represented by the following formula (I):

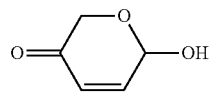

(I)

with an acylating agent and a hydrolase in a water-containing organic solvent to produce said acyloxypyranone compound represented by the formula (II),
wherein the hydrolase is a lipase obtained from *Candida cylindracea* or a lipase obtained from *Candida rugosa*; and
the water-containing organic solvent has a water content of 100 ppm to 8,000 ppm.

2. A method for producing an alkyne compound represented by the following formula (IV):

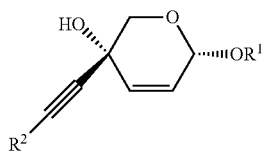

(IV)

wherein R¹ represents an acyl group, and R² represents a hydrogen atom or a tri-substituted silyl group, comprising:
reacting an acetylene organic metal compound represented by the following formula (III):

(III)

(wherein R² represents a hydrogen atom or a tri-substituted silyl group, and M represents an alkali metal atom, aluminum, or a magnesium monohalide) and a coordinating additive with the acyloxypyranone compound represented by formula (II) produced by the method according to claim 1 to produce said alkyne compound represented by formula (IV).

3. A method for producing a dihydrofuran compound represented by the following formula (V):

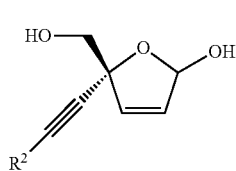

(V)

wherein R² has the same meaning as defined in formula (IV), comprising:
hydrolyzing, in the presence of an acid or a hydrolase, the alkyne compound represented by formula (IV) produced by the method according to claim 2 to produce said dihydrofuran compound represented by the formula (V).

4. The method for producing a dihydrofuran compound according to claim 3, wherein the yield of the obtained dihydrofuran compound is 91.9%.

5. The method for producing an alkyne compound according to claim 2, wherein the coordinating additive is an amine compound.

6. The method for producing an alkyne compound according to claim 2, wherein a stereoisomer ratio (target/diastereomer ratio) of the obtained alkyne compound is from 86/14 to 96/4.

7. The method for producing an alkyne compound according to claim 2, wherein a diastereomer, (2R,5S)-2-benzoyloxy-5,6-dihydro-2,4-pyrano-5-((trimethylsilyl)ethynyl)-5-ol is not obtained.

8. The method for producing an acyloxypyranone compound according to claim 1, wherein the acyl group of R¹ is a benzoyl group, and the acylating agent is benzoic acid, benzoic anhydride, or a benzoic acid ester.

9. The method for producing an acyloxypyranone compound according to claim 1, wherein the hydrolase is a lipase obtained from *Candida rugosa*.

10. A method for producing an alkyne compound represented by the following formula (IV):

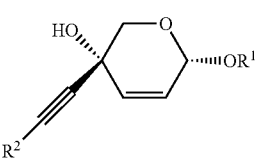

(IV)

wherein R¹ represents an acyl group, and R² represents a hydrogen atom or a tri-substituted silyl group, comprising:
reacting an acetylene organic metal compound represented by the following formula (III):

(III)

(wherein R² represents a hydrogen atom or a tri-substituted silyl group, and M represents an alkali metal atom, aluminum, or a magnesium monohalide) and a coordinating additive with an acyloxypyranone compound represented by the following formula (II):

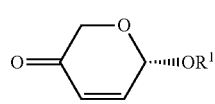

(II)

wherein R¹ represents an acyl group to produce said alkyne compound represented by formula (IV);
wherein the coordinating additive is an amine compound.

* * * * *